US008962063B2

(12) United States Patent
Smyth et al.

(10) Patent No.: US 8,962,063 B2
(45) Date of Patent: Feb. 24, 2015

(54) METHODS AND SYSTEMS FOR DOSING AND COATING INHALATION POWDERS ONTO CARRIER PARTICLES

(75) Inventors: Hugh D. C. Smyth, Austin, TX (US); Martin J. Donovan, Austin, TX (US)

(73) Assignee: ST.UNM, Albuquerque, NM (US)

( * ) Notice: Subject to any disclaimer, the term of this patent is extended or adjusted under 35 U.S.C. 154(b) by 237 days.

(21) Appl. No.: 13/389,558

(22) PCT Filed: Aug. 27, 2010

(86) PCT No.: PCT/US2010/047043
§ 371 (c)(1),
(2), (4) Date: Apr. 30, 2012

(87) PCT Pub. No.: WO2011/031564
PCT Pub. Date: Mar. 17, 2011

(65) Prior Publication Data

US 2012/0207913 A1 Aug. 16, 2012

Related U.S. Application Data

(60) Provisional application No. 61/237,347, filed on Aug. 27, 2009.

(51) Int. Cl.
*B05D 7/24* (2006.01)
*B05C 11/00* (2006.01)
*B05C 19/04* (2006.01)
*A61K 9/00* (2006.01)
(Continued)

(52) U.S. Cl.
CPC ............... *A61K 9/0075* (2013.01); *A61K 31/58* (2013.01); *A61K 9/14* (2013.01)
USPC ........... 427/2.14; 118/600; 118/620; 118/699

(58) Field of Classification Search
USPC .......................... 427/2.14; 118/600, 620, 699
See application file for complete search history.

(56) References Cited

U.S. PATENT DOCUMENTS 5,655,523 A 8/1997 Hodson et al.
8,196,576 B2 * 6/2012 Kriksunov et al. ...... 128/203.15
2002/0110527 A1 8/2002 Zhu et al.
(Continued)

FOREIGN PATENT DOCUMENTS

WO 02/087737 A1 11/2002
WO 2008/106616 A2 9/2008
WO WO 2009055030 A2 * 4/2009 ............ A61M 15/00

OTHER PUBLICATIONS

Takano et al., Particle design for dry powder inhalation via binderless powder coating by pressure swing granulation, Apr. 27, 2004, Powder Technology 141 (2004) 196-202.*
(Continued)

*Primary Examiner* — Dah-Wei D Yuan
*Assistant Examiner* — Hai Yan Zhang
(74) *Attorney, Agent, or Firm* — Kilpatrick Townsend & Stockton LLP

(57) ABSTRACT

A method of method of coating powdered medical agent onto a carrier particle for use in a dry powder inhaler may include applying ultrasonic energy to agglomerated powdered medical agent to deaggregate and aerosolize particles of the medical agent into particles having a desired average particle size, and coating at least one carrier particle with a desired amount of the deaggregated and aerosolized particles of the medical agent.

18 Claims, 7 Drawing Sheets

(51) Int. Cl.

| | |
|---|---|
| ***A61K 31/58*** | (2006.01) |
| *A61K 9/14* | (2006.01) |

(56) References Cited

U.S. PATENT DOCUMENTS

| | | | | |
|---|---|---|---|---|
| 2004/0009127 | A1 | 1/2004 | Musa et al. | |
| 2007/0125375 | A1 | 6/2007 | Finlay et al. | |
| 2007/0202053 | A1* | 8/2007 | Bilzi et al. | 424/46 |
| 2009/0101144 | A1 | 4/2009 | Gamard et al. | |
| 2010/0189878 | A1* | 7/2010 | Samburski et al. | 427/2.14 |

OTHER PUBLICATIONS

Sturtevant, Micronizer® Jet Mill, 2000, Sturtevant, Inc., Powder Processing Technology: The Sturtevant Solution.*

Yang et al., The effect of spray mode and chamber geometry of fluid-bed coating equipment and other parameters on an aqueous-based ethylcellulose coating, Oct. 26, 1992, International Journal of Pharmaceutics, vol. 86, Issues 2-3, pp. 247-257.*

Chow et al., Particle Engineering for Pulmonary Drug Delivery_ Expert Review, Mar. 2007, Pharmaceutical Research, vol. 24, No. 3, DOI: 10.1007/s11095-006-9174-3.*

International Search Report and Written Opinion of PCT/US2010/047043 mailed on May 23, 2011, 10 pages.

* cited by examiner

METHODS AND SYSTEMS FOR DOSING AND COATING INHALATION POWDERS ONTO CARRIER PARTICLES

CROSS-REFERENCE TO RELATED APPLICATIONS

This application claims the benefit of priority of U.S. Provisional Patent Application No. 61/237,347, filed on Aug. 27, 2009, the disclosure of which is incorporated herein by reference in its entirety.

TECHNICAL FIELD

The present disclosure relates to dry powder inhalers and, more particularly, to methods and systems for dosing and coating inhalation powders onto carrier particles.

BACKGROUND

The delivery of therapeutics to the lung for the local treatment of pulmonary disorders (asthma, chronic obstructive pulmonary disease (COPD), cystic fibrosis) has long been utilized, and inhalation therapy for the treatment of systemic diseases (e.g. diabetes) has been the focus of increasing academic and industry research within the past decade. Given its extremely large surface area, mild environment, and ease of administration, in contrast to oral and intravenous routes of drug delivery, the lung presents an especially attractive avenue of therapeutic delivery.

However, pulmonary drug delivery is not without its obstacles. For drug particles to deposit in the deep lung, where they exert their therapeutic action, they must possess certain physical properties. Specifically, the drug particles must have an average aerodynamic diameter below 5 microns, where the average aerodynamic diameter encompasses both the density and geometric diameter of the drug particle. Accordingly, aerosolized drug particles must be less than 5 microns in average aerodynamic diameter when they exit an inhaler to deposit in the deep lung. While both liquid (metered dose inhalers, nebulizers) and solid (dry powder inhalers) dosage forms are used for inhalation therapy, dry powder drug formulations are garnering an increasing share of the market due to their dose flexibility and excellent drug stability.

Dry powder formulations are generally binary mixtures comprised of fine drug particles (<5 microns) and coarse carrier particles (generally between 30 and 90 microns) blended together at a ratio of approximately 2% drug and 98% carrier (w/w). Due to the micron dimensions of the drug particles, the cohesive forces that exist between them, due primarily to Van der Waals and electrostatic forces, are quite strong and prevent drug particles from being readily deaggregated as they exit the inhaler. Even while the primary particle size (i.e., the size of a single particle of the drug powder) may be below 5 microns in diameter, a large fraction of the dose is agglomerated drug particles many times the size of the primary particles, leading to drug deposition in the mouth, throat, or upper airways, and possibly producing toxic side effects. The use of coarse carrier particles aids in the entrainment and dispersion of the formulation in the flow stream produced when a patient inhales through a dry powder inhaler.

Mixing the two component powders together is typically performed through a mechanical process, where the drug and carrier particles are placed in a metal or glass container, which is then spun and rotated in an orbital mixer for a period generally exceeding 30 minutes. The continuous contact between the drug and carrier particles serves to break apart drug aggregates and replace cohesive (drug-drug) interactions with adhesive (drug-carrier) interactions.

While dry powder formulations offer many advantages over liquid formulations, their performance is plagued by low drug delivery (generally below 30% of the total dose is delivered to the deep lung) and high throat and upper airway deposition. This is evidence that the majority of the drug particles exiting the inhaler are not in the primary particle size (<5 microns), but rather in agglomerates or still attached to carrier particles, which due to their large average aerodynamic diameter deposit in the throat and upper airways. Thus, the problems with blending drug and carrier particles through a mechanical process is that drug-drug cohesive interactions are not effectively eliminated, and press-on forces between drug and carrier particles can be large enough to prevent the detachment of the drug from the carrier particle during inhalation. Additionally, the use of mechanical processes to blend drug and carrier particles can also lead to milling of the drug particles, where the primary drug particles are fragmented during mixing, exposing high energy sites that bind tightly with either drug particles or carrier particles, preventing their dispersion.

A further problem arises when the size of the carrier particles is increased. For 2% drug/carrier particle blends (w/w) with carrier particles between 30 and 90 microns in diameter, the total surface area of the carrier particles is large enough to theoretically allow the fine drug particles to form a monolayer coating on the coarse carriers (although in practice many drug particles remain aggregated following blending). For powder of the same mass, as the size of the carrier is increased, the total surface area is reduced, and the drug can no longer form a monolayer of primary particles, and multiple layers of drug now coat the surface of the carriers. This is undesirable, as the strong cohesive interactions between the drug particles will preclude their dispersion into particles sized for deep lung delivery.

It may be desirable to provide a system and method for dosing and coating inhalation powders onto carrier particles that deaggregates drug powder into particles of primary size and reduces the presence and subsequent dispersion of drug agglomerates that could undesirably deposit in the mouth and upper airways. It may also be desirable to provide a system and method for coating carrier materials with drug particles sized to be deposited in the deep lung, improving the efficacy of current dry powder inhalers. It may also be desirable to provide a system and method that reduces the instances of tightly bound drug-carrier interactions.

SUMMARY OF THE INVENTION

According to various aspects of the disclosure, a method of coating active drug particle onto carrier particles for use in a dry powder inhaler may include applying ultrasonic energy to drug powder to deaggregate and aerosolize particles of the drug powder and coating carrier particles with the deaggregated and aerosolized particles of the drug powder.

In some aspects, the ultrasonic energy deaggregates the drug powder to particles having a primary particle size, for example, less than five microns. According to some aspects, the carrier particles may have a mean sieve diameter of 30-90 microns. According to some aspects, the carrier particles may have a mean sieve diameter greater than 500 microns.

DETAILED DESCRIPTION

Figure 1A:
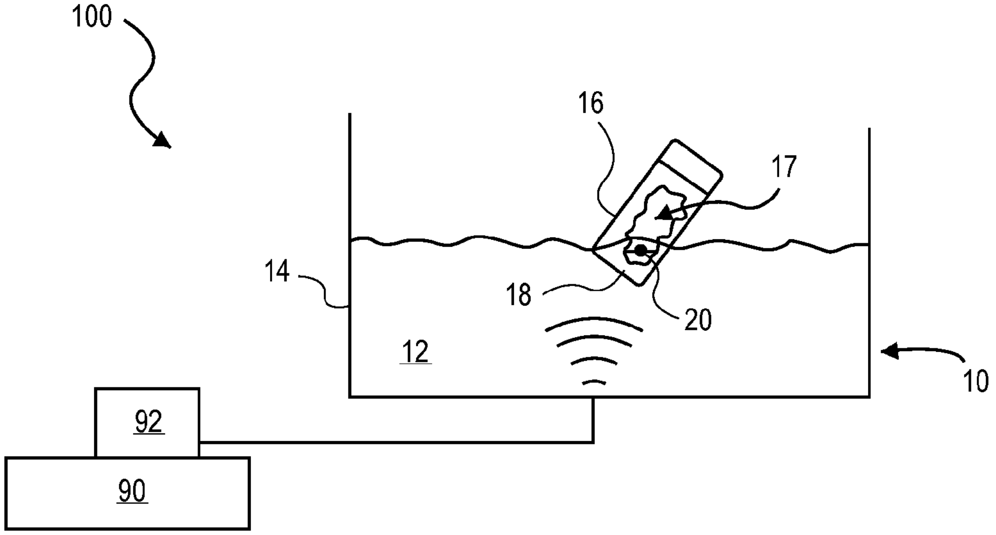
FIG. 1A is a schematic illustration of an ultrasonic cleaning bath for coating inhalations powders onto carrier particles in accordance with various aspects of the disclosure.
Figure 1B:
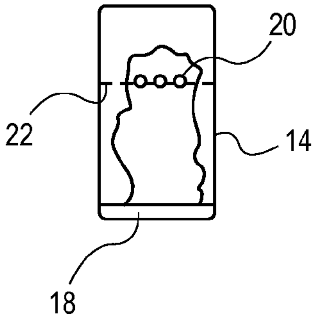
FIG. 1B is a schematic illustration of an exemplary vial for use with the bath of FIG. 1A.
Figure 1C:
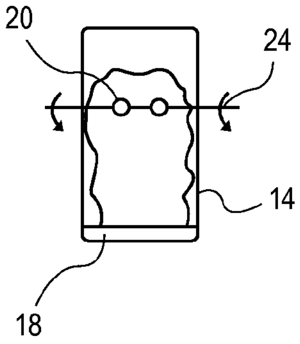
FIG. 1C is a schematic illustration of an exemplary vial for use with the bath of FIG. 1A.

FIGS. 1A-1C illustrates an example of a sonicating device 100 for coating inhalations powders onto a substrate, for example, carrier particles. The sonicating device 100 can be an ultrasonic device or a sonic device. For example, a sonic device may comprise a vessel immerged in a liquid, a loudspeaker or horn, a sound transducer, a solid surface coupled to any sonicating source, or the like.

In some aspects, the sonicating device 100 may comprise an ultrasonic bath 10, which may comprise any commercially available ultrasonic bath, such as for example, VWR Model 150T Sonicating Bath. In some aspects, the ultrasonic bath 10 may comprise a sonicator probe (not shown), for example, Misonix S4000 sonicating probe, which can be submerged into a vessel of fluid. In some aspects, the ultrasonic bath 10 may comprise a customized bath for the particular application of coating inhalation powder onto a substrate. In any event, the ultrasonic bath includes an energy source 90 and a controller 92 for applying sound energy, for example, ultrasound, to agitate a fluid 12 in a vessel 14. The sonicators may have adjustable power with maximum ratings from 100 up to 1500 Watts. The controller 92 may be operable to adjust the power of the sonicator, as well as the sound output frequency and amplitude.

The vessel 14 is configured to receive a vial 16 containing drug powder for use in inhalation treatment. The vial 16 contains a bed 18 of powdered medical agent. The powdered medical agent may comprise antiasthma agents, beta agonists, corticosteriods, antimicrobials, insulin, immune modulators/suppressors, chemo-therapeutic agents, anti-virals, prophylactics, vaccines, imaging agents, biologics, and the like. For example, the medical agent may be budesonide, salbutamol, ciprofloxacin, voriconazole, tobramycin, tacrolimus, etc. In some aspects, the agent may be micronized.

In various aspects, one or more substrate members 20 may be placed on the bed 18 of powdered medical agent, as shown in FIG. 1A. Thus, the bed 18 may be a support for the substrate member 20. The substrate 20 may comprise any of various materials capable of functioning as a carrier particle for medical agents, for example, for use in humans. The substrate 20 may be hydrophilic or hydrophobic; cationic, anionic, or neutral; polymeric (e.g. PLGA); a natural polymer (e.g. alginate, chitosan), a synthetic polymer (polyethylene glycol, polypropylene, polycarbonate, polystyrene, expanded polystyrene); a sugar (lactose, glucose, sucrose, maltodextrin); a protein (albumin); biodegradable or non-biodegradable; hygroscopic (silica gel); inorganic (calcium salts); gelatine capsules, hydroxypropyl methylcellulose capsules, or other capsule materials; glass; or waxes. The substrate 20 may comprise beads (spherical or non-spherical), flakes, or powders.

In some aspects, the substrate members 20 may be suspended a distance above the bed of powdered medical agent by a support 22. For example, the substrate members 20 may be suspended above the bed 18 of powdered medical agent by a support 22 that permits aerosolized particles of medical agent to reach the substrate members 20. In some aspects, the support 22 may comprise a mesh, screen, or perforated plate (FIG. 1B) comprising, for example, a stainless steel. In some aspects, the support may comprise a rotisserie member 24 associated with the vial 16 (FIG. 1C). According to various aspects, the rotisserie member 24 may be coupled to a drive member configured to rotate the rotisserie, as would be appreciated by persons skilled in the art. In some aspects, the substrate carrier material may be disposed in a container separate from the via 16, and the deaggregated and aerosolized particles of medical agent may be transported from the vial 16 using mild airflow to another container that contains the carrier substrate to be coated.

The vial 16 may be manually placed into the vessel 14, or the vessel 14 may be equipped with an automated mechanism for lowering the vial 16 into the bath 10, as would be understood by persons skilled in the art. A bottom portion of the vial 16 is placed in the fluid 12 of the sonicating bath 10 where ultrasonic energy deaggregates the micronized medical agent powders to a desired average particle size and causes a plume 17 of deaggregated and aerosolized particles of medical agent. In some aspects, about one-third to one-half of the vial 16 is lowered into the fluid 12 of the sonicating bath 10. It should be appreciated that more than one-half and less than one-third of the vial 16 may be lowered into the fluid 12 of the sonicating bath 10, depending on the amount of particles that a user intends to coat onto the substrate.

In some aspects, the desired average particle size may comprise an average aerodynamic diameter of 0.5 to 10 microns, or in some aspects, an average aerodynamic diameter of 0.5 to 5 microns. According to various aspects, the desired amount of particles to be coated on the substrate may comprise greater than 90% by number of particles having the desired average particle size. In some aspects, the desired amount of particles to be coated on the substrate may comprise greater than 70% by weight of particles having the desired average particle size.

In one exemplary embodiment, 2 milligrams of drug powder (primary particle size <5 microns) are placed into a 30 mL capacity glass vial. The vial is lowered into an ultrasonic cleaning bath filled with water, such that the bottom half of the vial containing the drug powder is submerged below the fluid. The ultrasonic energy causes the powder to become fluidized, where primary particles are detached from each other and dispersed throughout the vial, forming a cloud of primary drug particles. In the presence of a substrate acting as a drug carrier (e.g. coarse powder, polystyrene beads (>1 mm diameter), or polymer films), the drug coats the carrier material with particles of primary size.

The carrier material may comprise particles of any size, ranging from the smallest available carrier size to the largest available carrier size. For example, according to various aspects, the carrier particles may have a mean sieve diameter of 30-90 microns. According to some aspects, the carrier particles may have a mean sieve diameter greater than 500 microns, even exceeding 5 mm and possibly as large as 10 mm.

In contrast with the standard blending of drug and carrier through mechanical processes, the drugs particles and carrier particles are not continuously rubbed together, and the drug particles do not have the opportunity to orient themselves such that the cohesive force between them is maximized (e.g. through the contact of high energy sites on the surface of the drug and carrier particles), allowing for more effective dispersion of drug particles in their primary size. Ultrasonic energy is an inexpensive and readily available source of energy that effectively deaggregates drug powders into their primary particle size.

Deaggregation of drug powder into particles of primary size reduces the presence, and subsequent dispersion, of drug agglomerates that could undesirably deposit in the mouth and upper airways. Carrier materials may be coated with the deaggregated drug powder comprising drug particles sized to be deposited in the deep lung, thereby improving the efficacy of current dry powder inhalers.

Use of ultrasonic energy to deaggregate drug powders may also reduce the instances of tightly bound drug-carrier interactions by eliminating, for example, the press-on forces that occur when powder is tumbled in an orbital mixer. Ultrasonic energy may also reduce the instances where the drug particles are localized to the high energy sites on the surface of the carriers.

Press-on forces occur when powder is tumbled in an orbital mixer. As the strength of the press-on forces is proportional to the contact area between the drug and carrier particles, compression of the drug and carrier during mixing via mechanical processes maximizes the contact area between them. As a result, the strength of the interactions between drug and carrier is increased and the amount of drug delivered to the deep lung is reduced.

Drug particles are localized to the high energy sites on the surface of the carriers as the drug and carriers rub together continuously during mixing through a purely mechanical process. Drug attached to these high energy sites are more difficult to detach from the carriers, thus reducing the performance of the dry powder formulation.

Systems and methods for dosing and coating inhalation powders onto carrier particles in accordance with this disclosure may overcome one or more of the aforementioned disadvantages of traditional mechanical mixing devices.

Figure 2:
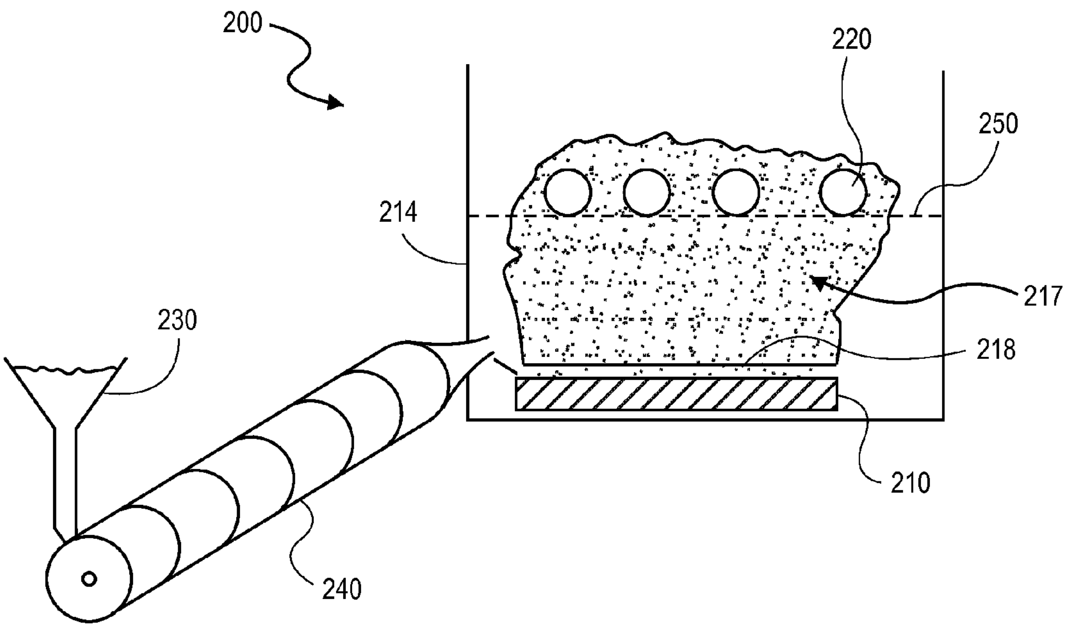
FIG. 2 is a schematic illustration of a sonicating device for coating inhalations powders onto carrier particles in accordance with various aspects of the disclosure.

FIG. 2 illustrates an example of a sonicating device 200 for coating powdered medical agent, for example, inhalation powders, onto a substrate 220, for example, one or more carrier particles, in accordance with various aspects of the disclosure. The device 200 includes a sonicating member 210 configured to deaggregate and aerosolize powdered medical agent into a desired average particle size. The sonicating member 210 may include a sonicating plate or probe, or the region 210 may comprise a material that conducts sound or ultrasound. The device 200 may include a supply member 230, such as for example, a gravity-fed hopper or the like, and a feeding member 240, such as, for example, a screw feeder.

The supply member 230 may be structured and arranged to supply powdered medical agent to the feeding member 240, and the feeding member 240 may be operable to feed agglomerated powdered medical agent to the sonicating member 210. At the sonicating member 210, the powdered medical agent may be deaggregated and aerosolized into a plume 217 of particles having a desired average particle size. The aerosolized particles 217 may then be coated onto one or more carrier particles 220 positioned above the sonicating member 210.

In some aspects, the carrier particles 220 may be held above the sonicating member 210 by a support 250, such as, for example, a mesh, a screen, a support bar, a perforated plate, a rotisserie, or the like. In various aspects, the support may comprise a movable support 250, for example, a screen, a mesh, a perforated plate, or the like, configured to transport the carrier particles 220 a region of the plume 217 above the sonicating member 210, as would be appreciated by persons skilled in the art. The coated carrier particles may be then removed from the sonicating region and directed to another station of a manufacturing and/or packaging process via the movable support 250, as would understood by persons skilled in the art.

Figure 3:
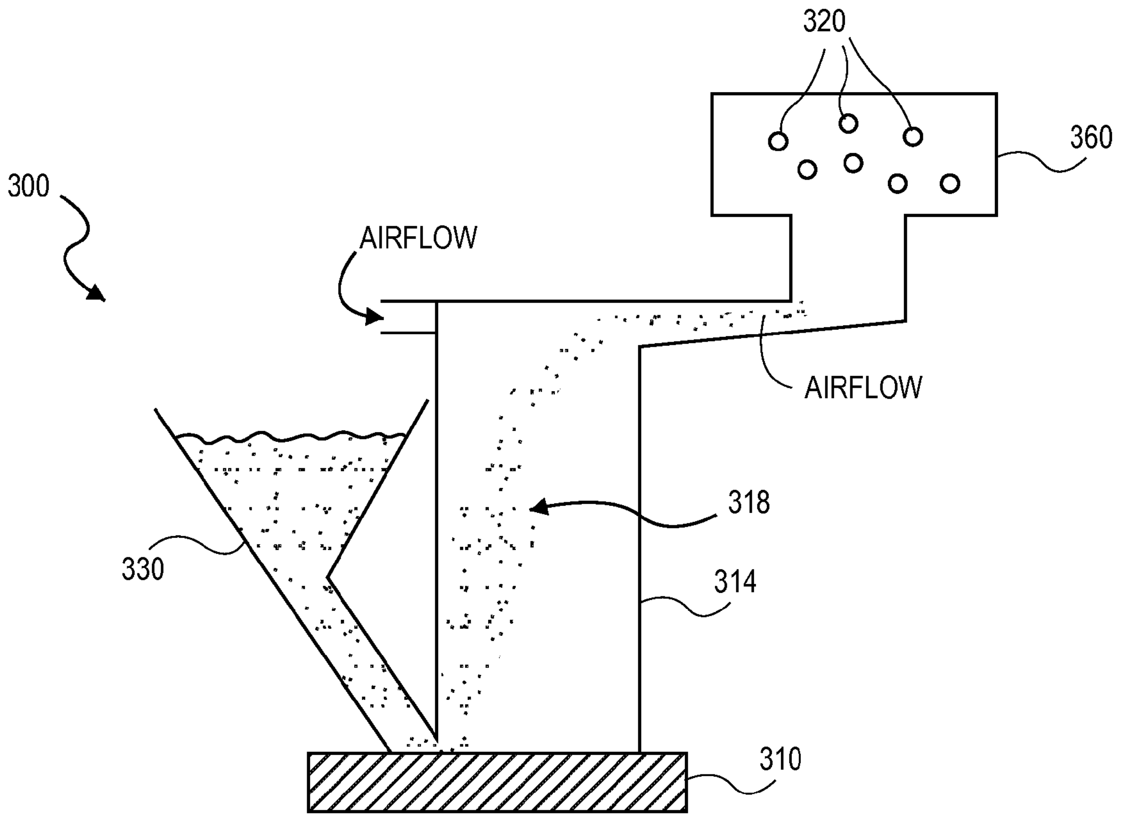
FIG. 3 is a schematic illustration of a piezoelectric device for aerosolizing powder for coating onto carrier particles in accordance with various aspects of the disclosure.

FIG. 3 illustrates an example of a sonicating device 300 for coating inhalation powders onto a substrate 320, for example, one or more carrier particles, in accordance with various aspects of the disclosure. The device 300 may comprise a piezoelectric device 310 for deaggregating and aerosolizing powdered medical agent into particles having a desired average particle size for coating onto one or more carrier particles 320. As shown, powdered medical agent may be fed from a drug supply member 330, such as for example, a gravity-fed hopper or the like to the piezoelectric plate 310 in a chamber 314. The piezoelectric plate 310 deaggregates and aerosolizes the powdered medical agent so that a plume 318 of the deaggregated and aerosolized particles can be carried out of the chamber 314 by airflow provided at the top of the chamber 314. The deaggregated particles may be transported from the deaggregation chamber 314 via the airflow and can be introduced to carrier particles 320 that are housed within a coating chamber 360. The carrier particles 320 may also be fluidized in the coating chamber 360 using an air flow as is normally done in a fluidized bed that is commonly employed in pharmaceutical processing and as would be understood by persons skilled in the art. In some aspects, the carrier particles 320 may be suspended in the coating chamber 360 via a support (not shown).

According to some aspects, the deaggregated particles may be directly transported to a patient using a tube and mouthpiece adaptor (not shown), similar to a conventional liquid nebulizer arrangement. However, in the present situation, the aerosol is not a liquid aerosol but a dry powder aerosol which has many of the advantages already mentioned such as dose payload, stability, and dosing times.

According to various aspects of the disclosure, the use of ultrasonics to load drug onto the carrier materials may compensate for vastly reduced surface area of large carrier particles compared to lactose carrier particles. For standard dry powder formulations comprised of 2% drug (w/w) with 98% lactose carrier particles (diameter <90 microns), the total surface area of the lactose carriers is sufficient to theoretically allow for a monolayer of drug to coat the surface of the carriers. As the size of the carriers is increased, the surface area is no longer sufficient to support a monolayer of drug particles, and cohesive forces from drug-drug interactions produce agglomerates that deposit in the throat and upper airways during inhalation. However, by treating the drug powder with ultrasonic energy, the aggregated powder is dispersed into primary particles, which then coat the surface of the carrier particles. While the reduced surface area of the carrier particles will preclude the formation of a drug monolayer, dispersing the drug into primary particles will disrupt any high energy bonding sites between adjacent drug particles, and when they deposit on the carrier particle following ultrasonic deaggregation, drug particles will not have the opportunity to orient themselves so as to maximize the strength of their cohesive interaction, allowing for increased dispersion of primary particles and enhanced deep lung deposition.

Example 1

Bead Carrier Particles

Carrier particles, comprised of low density (<0.300 g/$cm^3$) polystyrene beads, with geometric diameter between 4.35 and 5.35 microns were placed into a glass vial (25 mL volume capacity) with micronized budesonide ($d_{90}$<5 microns) as the active pharmaceutical ingredient. 1 polystyrene bead was placed into a vial in addition to 1 milligram of budesonide powder. The vial was lowered into an ultrasonicating water bath such that the section of the vial containing the drug and carrier particles was submerged beneath the water. When the ultrasonics were initiated, the budesonide powder was fluidized and aerosolized within the vial (it must be noted that the top of the vial was covered, preventing the escape of the aerosolized drug). The ultrasonics served to disperse the budesonide from an aggregated powder into individual primary particles of drug. These primary particles were aerosolized and dispersed throughout the vial, which deposited on the polystyrene carrier particle. Following three minutes, the ultrasonics were turned off, and the vial was removed from the water bath. A single budesonide-coated polystyrene bead was placed into the capsule chamber of an Aerolizer dry powder inhaler, which was connected to a Next Generation Cascade Impactor. In vitro drug dispersion studies were performed at a volumetric flow rate of 60 L/min for 4 seconds. The budesonide remaining on the polystyrene carrier, or depositing on the inhaler, throat, pre-separator, and stages 1-8 of the cascade impactor was collected and quantified.

The amount of drug loaded onto a single polystyrene carrier particle ranged from 360-480 micrograms, comparable to the 400 micrograms loaded in a standard 20 mg dose of 2% (w/w) drug/lactose carrier formulation. The respirable fraction (the fraction of the total dose that deposits in the deep lung) for the polystyrene carrier particles ranged between 45 and 50%. The respirable fraction from standard lactose carrier particles is generally below 25%.

Example 2

Flake Carrier Particles

Carrier particles were prepared in the following method. Flake-shaped carrier particles between 1 and 3 millimeters in length, 1 and 3 millimeters in width, 100 microns in thickness and composed of hydroxypropyl methylcellulose (HPMC) were obtained by fragmenting a HPMC two-piece capsule. The general shape of the resulting capsule fragments were of irregular quadrilaterals, fitting the above dimensions, although a more accurate description would be that they were polygons with non-uniform sides (both in length and number), and angles. 32.4 milligrams of HPMC carrier particles (the collective fragments of 1 piece of the original 2 piece capsule, capsule size 1) were placed into a glass vial (25 mL volume capacity). Added to this was 2 milligrams of micronized budesonide powder (primary particle size=$d_{90}$<5 microns) as the active pharmaceutical ingredient. The vial was lowered into an ultrasonicating water bath such that the section of the vial containing the drug and carrier particles was submerged beneath the water. When the ultrasonics were initiated, the budesonide powder was fluidized and aerosolized within the vial (it must be noted that the top of the vial was covered, preventing the escape of the aerosolized drug). The ultrasonics served to disperse the budesonide from an aggregated powder into individual primary particles of drug. These primary particles were aerosolized and dispersed throughout the vial, which deposited on the HPMC carrier particles. Following three minutes, the ultrasonics were turned off, and the vial was removed from the water bath. The budesonide-coated HPMC fragments were placed into the capsule chamber of an Aerolizer dry powder inhaler, which was connected to a Next Generation Cascade Impactor. In vitro drug dispersion studies were performed at a volumetric flow rate of 60 L/min for 4 seconds. The budesonide remaining on the HPMC carriers, or depositing on the inhaler, throat, pre-separator, and stages 1-8 of the cascade impactor was collected and quantified.

The amount of drug loaded on the HPMC particles was 1.235 milligrams. Standard dry powder formulations with lactose carrier particles (<90 micron diameter) generally load 400 micrograms (0.400 milligrams) of drug. The fine particle fraction (the percent of the dose emitted from the inhaler that deposits in the deep lung) was 78%, compared to less than 30% for standard lactose carrier particles. This example illustrates that the shape of the carrier particle is not restricted to spherical beads. The mechanism of action describes a carrier particle that is retained within the dry powder inhaler device during inhalation, allowing for a wide range of materials, sizes and morphologies to be employed as drug carriers in dry powder formulations.

Example 3

Approximately 2 milligrams of micronized budesonide drug powder ($d_{50}$=2.10 micrometer) were placed in a 30-mL glass scintillation vial (1.5-mm wall thickness), into which was added a spherical polystyrene bead (approx. diameter: 4.5-6 mm). The lower portion (approx. one-half to one-third) of the glass vial was submerged below the water level in an ultrasonic cleaner (operating frequency=35 kHz). The ultrasonic cleaner was turned on for 2 minutes, causing the powdered drug to become dispersed into primary particle sizes (between 1-5 um) and aerosolized within the vial. As the aerosolized drug plume continuously passed over/around the polystyrene bead, drug particles deposited onto the surface of the bead and remained attached through interparticle forces (e.g. van der Waals interactions)

Figure 4:
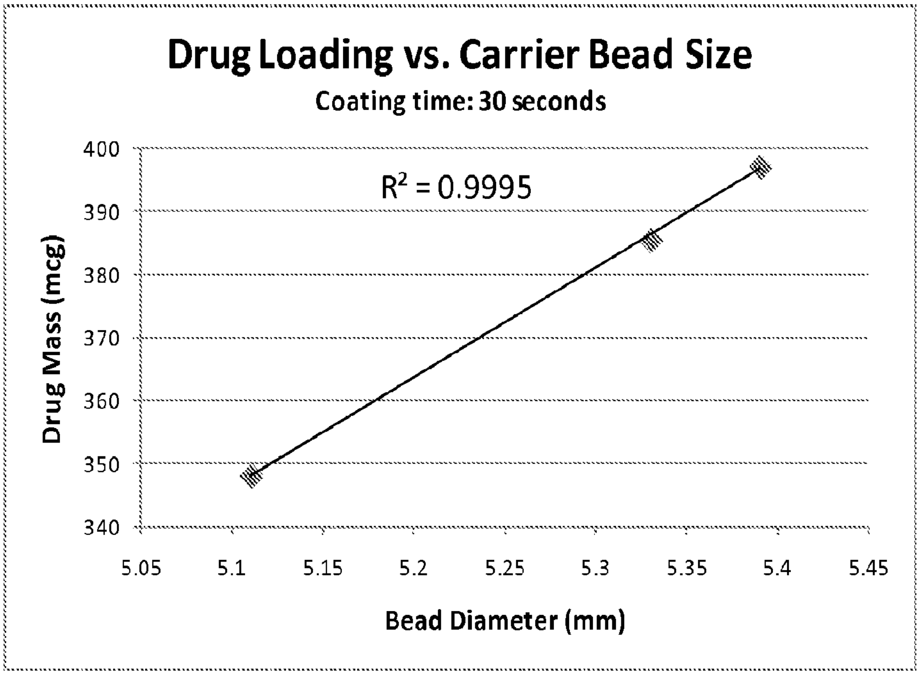
FIG. 4 is a graph of drug mass loaded/coated onto the surface of a carrier particle plotted against the bead diameter for a 30-second coating interval.

Referring now to FIG. 4, the mass of drug particle that is loaded/coated onto the surface of a polystyrene bead (carrier particle) plotted against the diameter of the bead for a 30-second coating interval. The mass of drug coated onto the surface of the bead is correlated to the size of the bead, allowing control of the administered drug dose.

Figure 5:
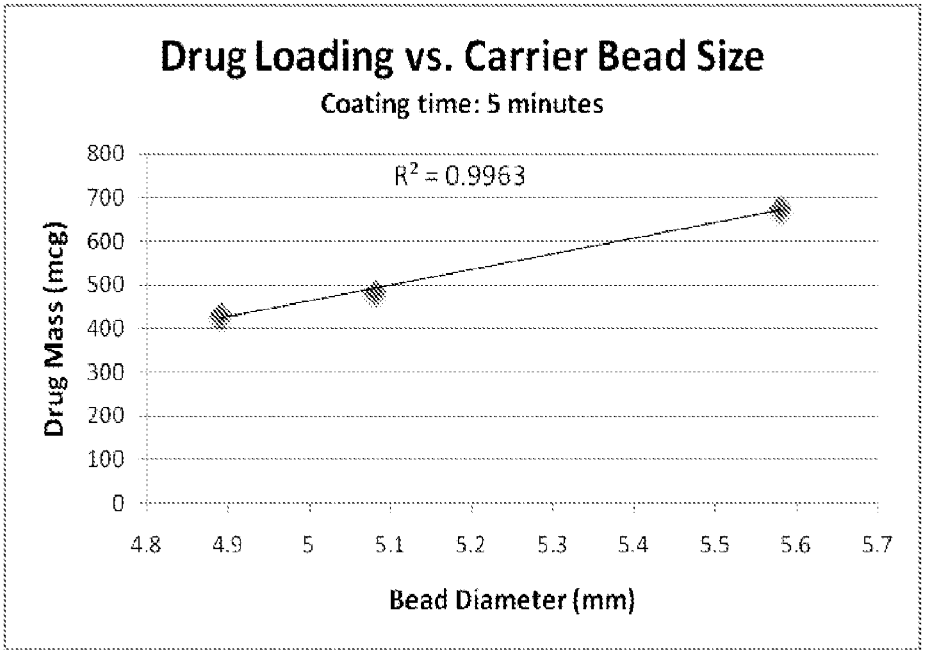
FIG. 5 is a graph of drug mass loaded/coated onto the surface of a carrier particle plotted against the bead diameter for a 5-minute coating interval.

FIG. 5 illustrates the mass of drug particle that is loaded/coated onto the surface of a polystyrene bead (carrier particle) plotted against the diameter of the bead for a 5-minute coating interval. The mass of drug coated onto the surface of the bead is correlated to the size of the bead, allowing control of the administered drug dose.

Figure 6:
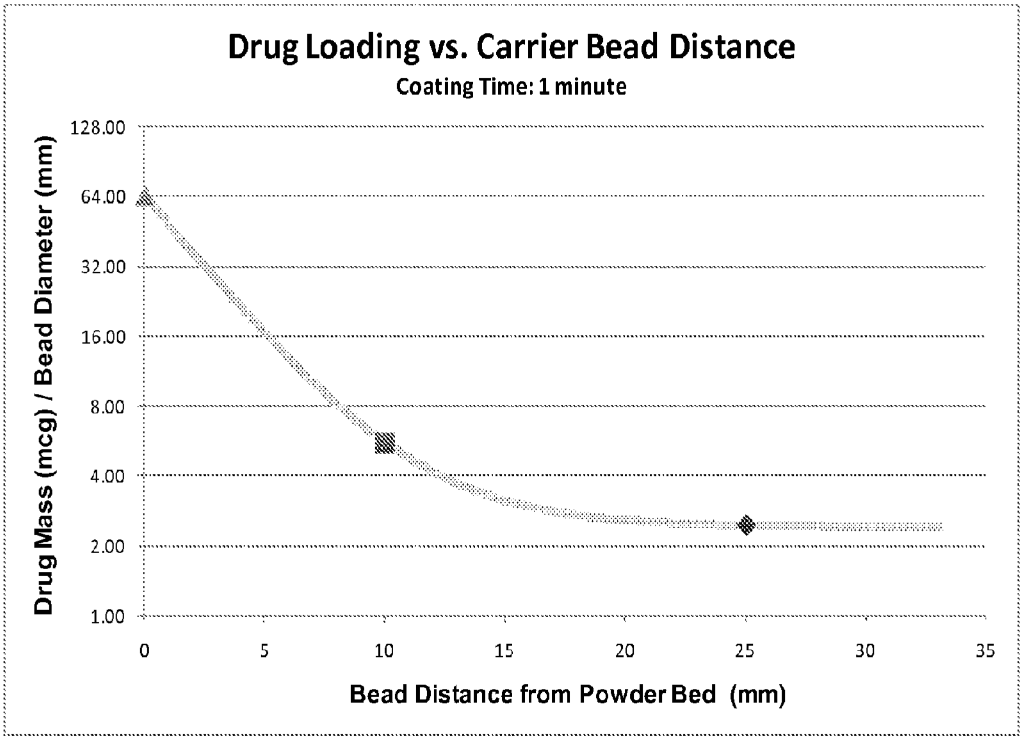
FIG. 6 is a graph of drug mass per bead diameter loaded/coated onto the surface of a carrier particle plotted against the bead distance from a powder bed for a 1-minute coating interval.

Referring now to FIG. 6, the mass of drug (mcg) that is loaded/coated onto the surface of a polystyrene bead (carrier particle) per bead diameter (mm) is plotted against the distance of the bead from the powder in the scintillation vial for a 5-minute coating interval. At a distance of 0 mm the bead was placed directly on the powder bed. By adjusting the distance of the bead from the drug sample, for example, by suspending the bead above the bed of drug powder via a support or the like, the total mass coated onto the surface can be varied, as shown in FIG. 6.

Figure 7:
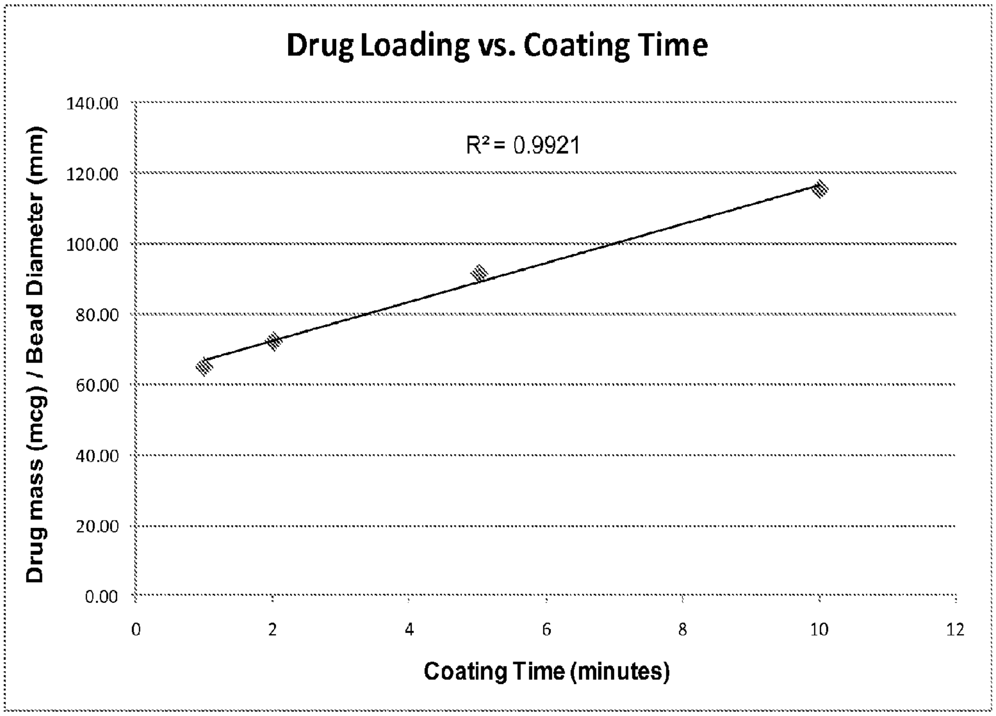
FIG. 7 is a graph of drug mass per bead diameter loaded/coated onto the surface of a carrier particle plotted against the coating time.

FIG. 7 illustrates the mass of drug (mcg) that is loaded/coated onto the surface of a polystyrene bead (carrier particle) per bead diameter (mm) plotted against the time of the drug coating process. By varying the time of the coating process, the amount of drug loaded onto the surface of a carrier bead can be controlled.

Figure 8:
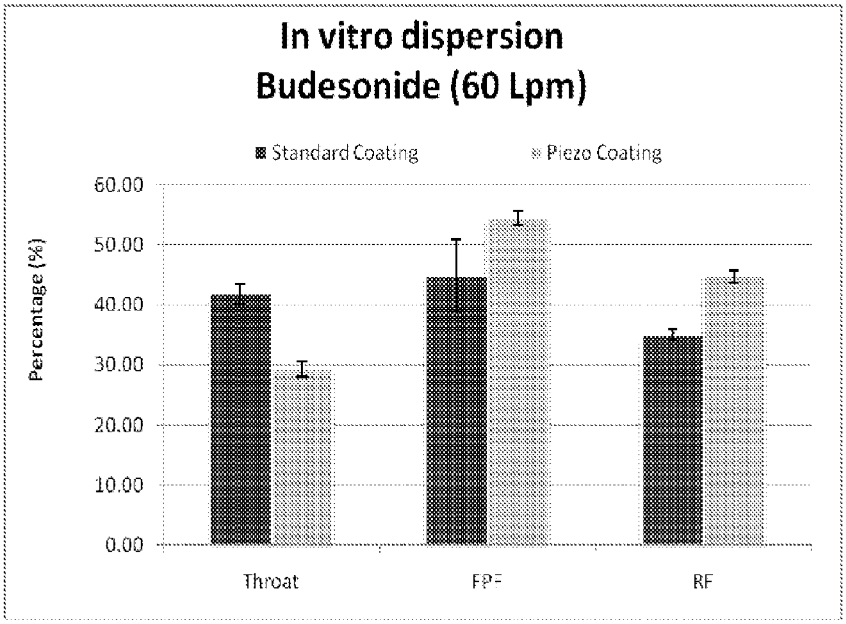
FIG. 8 is a graph of in vitro drug deposition performance of 5 mm polystyrene beads coated with micronized budesonide.

FIG. 8 illustrates the in vitro drug deposition performance of 5 mm polystyrene beads coated with micronized budesonide was evaluated. Drug loading/coating performed by the standard method traditionally employed to blend lactose/drug formulations was compared with drug loading/coating through the aerosolized powder coating technique of the present disclosure; that is, where drug is aerosolized by ultrasonic energy induced by piezoelectric vibrations (piezo coating).

For the standard coating method, 2-mg of micronized budesonide and a polystyrene bead were added to a 30-mL glass scintillation vial. The sample vial was placed in a Turbula orbital shaker for 40 minutes at 46 RPM.

For the aerosolized powder coating method consistent with the present disclosure, 2-mg of micronized budesonide and a polystyrene bead were added to a 30-ml glass scintillation vial.). The lower portion (approx. one-half to one-third) of the glass vial was submerged below the water level in an ultrasonic cleaner (operating frequency=35 kHz). The ultrasonic cleaner was turned on for 2 minutes, causing the powdered drug to become dispersed into primary particle sizes (between 1-5 μm) and aerosolized within the vial. As the aerosolized drug plume continuously passed over/around the polystyrene bead, drug particles deposited onto the surface of the bead and remained attached through inter-particle forces (e.g. van der Waals interactions).

The standard coating method resulted in significant drug aggregation on the surface of the polystyrene bead. These aggregates were not completely dispersed during aerosolization, accounting for the relatively large throat deposition (>40%) and low overall deep lung deposition (as defined by the respirable fraction, RF). By comparison, the aerosolized powder coating method markedly reduced the formation of aggregated drug clusters on the surface of the polystyrene bead. This reduced level of drug aggregation was reflected in the lower overall throat deposition (<30%) and higher deep lung deposition relative to the standard coating technique.

Figure 9A:
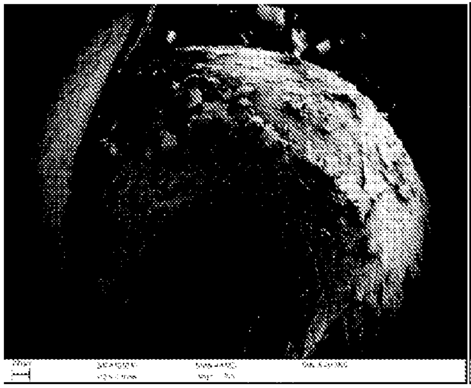
FIGS. 9A and 9B are photographic illustrations of polystyrene beads coated with micronized budesonide by a standard coating method.
Figure 9B:
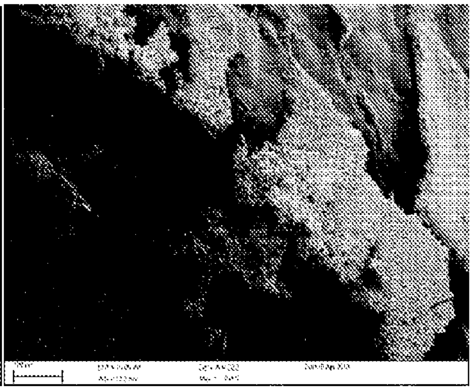
Figure 10A:
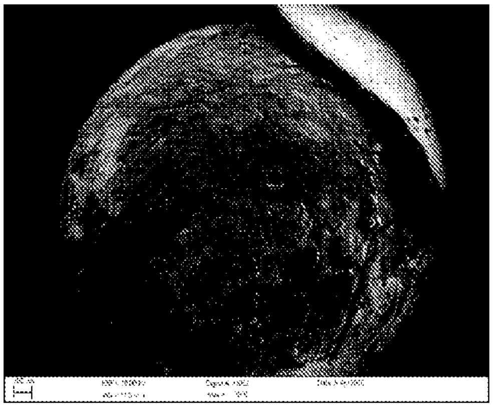
FIGS. 10A and 10B are photographic illustrations of polystyrene beads coated with micronized budesonide by an aerosolized powder coating method according to the disclosure.
Figure 10B:
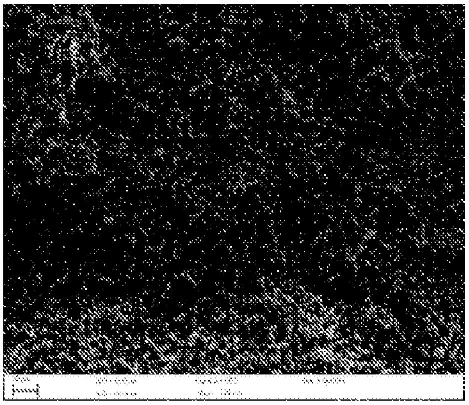

FIGS. 9A and 9B illustrate polystyrene beads coated with micronized budesonide by the standard coating method, while FIGS. 10A and 10B illustrate polystyrene beads coated with micronized budesonide by the aerosolized powder coating method disclosed herein. As is evident from these microscopy (i.e., scanning electron microscopy) images, drug particles on the substrate are significantly less aggregated and more loosely bound using the coated method disclosed herein (FIGS. 10A and 10B) as compared with the conventional coating method (FIGS. 9A and 9B). This is desirable for dry powder formulations where the ultimate goal is to remove the drug particles from the substrate surfaces during inhalation.

It should be appreciated that nasal aerosols are increasingly popular methods for drug delivery. The nasal route is a non-invasive way of administering drugs with rapid uptake into the bloodstream and is considered to be important for the systematic delivery of proteins and other macromolecules. The particle size distribution is a key parameter in defining the efficiency of nasal aerosol delivery and is a predictor of the deposition site for the drug within the nasal passages.

To increase nasal deposition and minimize deposition in the lungs and gastro-intestinal tract, aerosol particles should generally have an average aerodynamic diameter greater than 10 to 20 microns. Below this range reduced naso-pharyngeal deposition and increased pulmonary deposition occurs. These particles are also subject to adhesive forces and therefore controlled deposition on the substrate is very useful and will enhance the efficiency of delivery into the nasal cavity. In addition, deaggregated powders are more likely to coat the nasal passages more uniformly compared to aggregated powders.

Particles <10 μm have the potential to be deposited in the lower respiratory tract if inhaled. This can lead to issues with potential toxicities as well as reduce the dose fraction reaching the intended site of delivery. Particles that are too large and/or in too high of a mass may not dissolve efficiently on the nasal mucosa. Therefore a desired average particle size range is between 10 and 145 microns. A person skilled in the art would understand that the systems and methods described herein can be adapted to provide the desired average particle size for nasal inhalation applications.

It will be apparent to those skilled in the art that various modifications and variations can be made to the methods and systems for dosing and coating inhalation powders onto carrier particles of the present disclosure without departing from the scope of the invention. Other embodiments of the invention will be apparent to those skilled in the art from consideration of the specification and practice of the invention disclosed herein. It is intended that the specification and examples be considered as exemplary only.

The invention claimed is:

1. A method of coating powdered medical agent onto a substrate for use in a dry powder inhaler, the method comprising:

applying energy to agglomerated powdered medical agent particles to deaggregate and aerosolize the particles of the medical agent at a first location, wherein the energy comprises at least one of ultrasonic energy, sonic energy, and piezoelectric energy;

introducing from a second location that is separate from and spaced-apart relative to the first location a substrate comprising a plurality of discrete carrier particles to the deaggregated and aerosolized particles of the medical agent such that the carrier particles are introduced to the medical agent particles while the medical agent particles are deaggregated and aerosolized; and coating the plurality of discrete carrier particles with the deaggregated and aerosolized particles of the medical agent.

2. The method of claim 1, further comprising controlling a dose of particles of medical agent applied to the carrier particles by changing the size of the carrier particles.

3. The method of claim 1, further comprising controlling a dose of particles of medical agent applied to the carrier particles by changing the distance at which the carrier particles are positioned relative to a bed of the agglomerated powdered medical agent particles to be deaggregated and aerosolized.

4. The method of claim 1, further comprising controlling a dose of particles of medical agent applied to the carrier particles by changing the time period during which the coating step is carried out.

5. The method of claim 1, wherein the medical agent particles have an average particle size of less than ten microns.

6. The method of claim 5, wherein the average particle size is less than five microns.

7. The method of claim 1, wherein the carrier particles have a mean sieve diameter less than or equal to 500 microns.

8. The method of claim 7, wherein the carrier particles have a mean sieve diameter of 30-90 microns.

9. The method of claim 1, wherein the carrier particles have a mean sieve diameter of 500-10,000 microns.

10. The method of claim 1, wherein the amount of the deaggregated and aerosolized particles of the medical agent coated on the carrier particles is at least about 70% by weight of the average aerodynamic diameter.

11. The method of claim 1, wherein the amount of the deaggregated and aerosolized particles of the medical agent coated on the carrier particles is at least about 90% by number of the average aerodynamic diameter.

12. The method of claim 1, wherein the introducing step comprises transporting the deaggregated and aerosolized medical agent particles to the carrier particles using airflow.

13. A method of coating powdered medical agent onto a substrate for use in a dry powder inhaler, the method comprising:

applying energy to agglomerated medical particle agents to deaggregate and aerosolize the medical particle agents at a first location, wherein the energy comprises at least one of ultrasonic energy, sonic energy, and piezoelectric energy; and while in their deaggregated and aerosolized state, introducing from a second location that is separate from and spaced-apart relative to the first location a plurality of discrete and separated carrier particles to the medical particle agents such that the carrier particles are introduced while the medical agent particles are deaggregated and aerosolized to coat the carrier particles with the medical particle agents.

14. The method of claim 13, wherein the deaggregated and aerosolized medical agent particles are introduced to the carrier particles using airflow.

15. The method of claim 13, wherein the carrier particles are contained in a fluidization bed, and passing air up through the bed to fluidize the carrier particles, and wherein the deaggregated and aerosolized medical agent particles are introduced to the fluidized carrier particles to coat the medical agent particles on the carrier particles.

16. The method as in claim 13, further comprising placing the coated carrier particles into an aerosolization device that is configured, when operated, to remove the medical particle agents from the carrier particles.

17. A method of coating powdered medical agent onto a substrate for use in a dry powder inhaler, the method comprising:

applying energy to agglomerated medical particle agents to deaggregate and aerosolize the medical particle agents at a first location, wherein the energy comprises at least one of ultrasonic energy, sonic energy, and piezoelectric energy;

while in their deaggregated and aerosolized state, introducing from a second location that is separate from and spaced-apart relative to the first location discrete and separated carrier particles to the medical particle agents such that the carrier particles are introduced to the medical agent particles while the medical agent particles are deaggregated and aerosolized to coat the carrier particles with the medical particle agents; and packaging the coated carrier particles.

18. The method as in claim 17, further comprising placing the coated carrier particles into an aerosolization device that is configured, when operated, to remove the medical particle agents from the carrier particles.

* * * * *

UNITED STATES PATENT AND TRADEMARK OFFICE

CERTIFICATE OF CORRECTION

PATENT NO. : 8,962,063 B2
APPLICATION NO. : 13/389558
DATED : February 24, 2015
INVENTOR(S) : Hugh D. C. Smyth et al.

It is certified that error appears in the above-identified patent and that said Letters Patent is hereby corrected as shown below:

In the Title Page of the Patent:

Item 73, please delete "ST.UNM" and insert --STC.UNM--.

Signed and Sealed this
Twenty-eighth Day of July, 2015

Michelle K. Lee
*Director of the United States Patent and Trademark Office*